United States Patent
Feurer et al.

(10) Patent No.: US 6,733,122 B1
(45) Date of Patent: May 11, 2004

(54) OPTICAL SYSTEM, IN PARTICULAR INTRAOCULAR LENS, CONTACT LENS

(75) Inventors: Bernard Feurer, Montlaur (FR); Monique Mauzac, Toulouse (FR)

(73) Assignee: Ioltech, La Rochelle (FR)

( * ) Notice: Subject to any disclaimer, the term of this patent is extended or adjusted under 35 U.S.C. 154(b) by 0 days.

(21) Appl. No.: 09/647,546

(22) PCT Filed: Apr. 1, 1999

(86) PCT No.: PCT/FR99/00764

§ 371 (c)(1),
(2), (4) Date: Nov. 29, 2000

(87) PCT Pub. No.: WO99/52009

PCT Pub. Date: Oct. 14, 1999

(30) Foreign Application Priority Data

Apr. 2, 1998 (FR) .............................. 98 04109

(51) Int. Cl.$^7$ ................................. G02C 7/04
(52) U.S. Cl. ................. 351/160 R; 623/6.37; 623/6.56
(58) Field of Search ............ 351/159, 160 R, 351/160 H, 161–162, 177; 623/6.37, 6.56, 6.11, 6.13, 6.22

(56) References Cited

U.S. PATENT DOCUMENTS

| | | | | | |
|---|---|---|---|---|---|
| 3,800,594 | A | * | 4/1974 | Hutchings et al. | 73/514.27 |
| 4,373,218 | A | * | 2/1983 | Schachar | 623/6.13 |
| 4,842,601 | A | * | 6/1989 | Smith | 623/6.34 |
| 5,136,669 | A | * | 8/1992 | Gerdt | 385/39 |
| 5,172,143 | A | | 12/1992 | Baude et al. | 351/177 |
| 5,258,024 | A | | 11/1993 | Chavel et al. | 623/5.16 |
| 5,731,909 | A | * | 3/1998 | Schachar | 359/676 |

FOREIGN PATENT DOCUMENTS

EP  0 407 294  1/1991

OTHER PUBLICATIONS by Y. Koike et al., "Gradient–index contact lens", *Applied Optics*, vol. 34, No. 22, Aug. 1995, pp. 4669–4673.

* cited by examiner

Primary Examiner—Jordan M. Schwartz
(74) Attorney, Agent, or Firm—Young & Thompson

(57) ABSTRACT

Intraocular lenses, for example intraocular implants, contact lenses and the like. The optical system is made of a material whereof the refractive index varies along at least one given direction, this material being a homogeneous material with variable index according to its chemical composition or by the action of mechanical effects, or a heterogeneous material with different molecular orientations. The invention is useful for making lenses with accommodative sighting.

36 Claims, 1 Drawing Sheet

OPTICAL SYSTEM, IN PARTICULAR INTRAOCULAR LENS, CONTACT LENS

FIELD OF THE INVENTION

Figure 1:
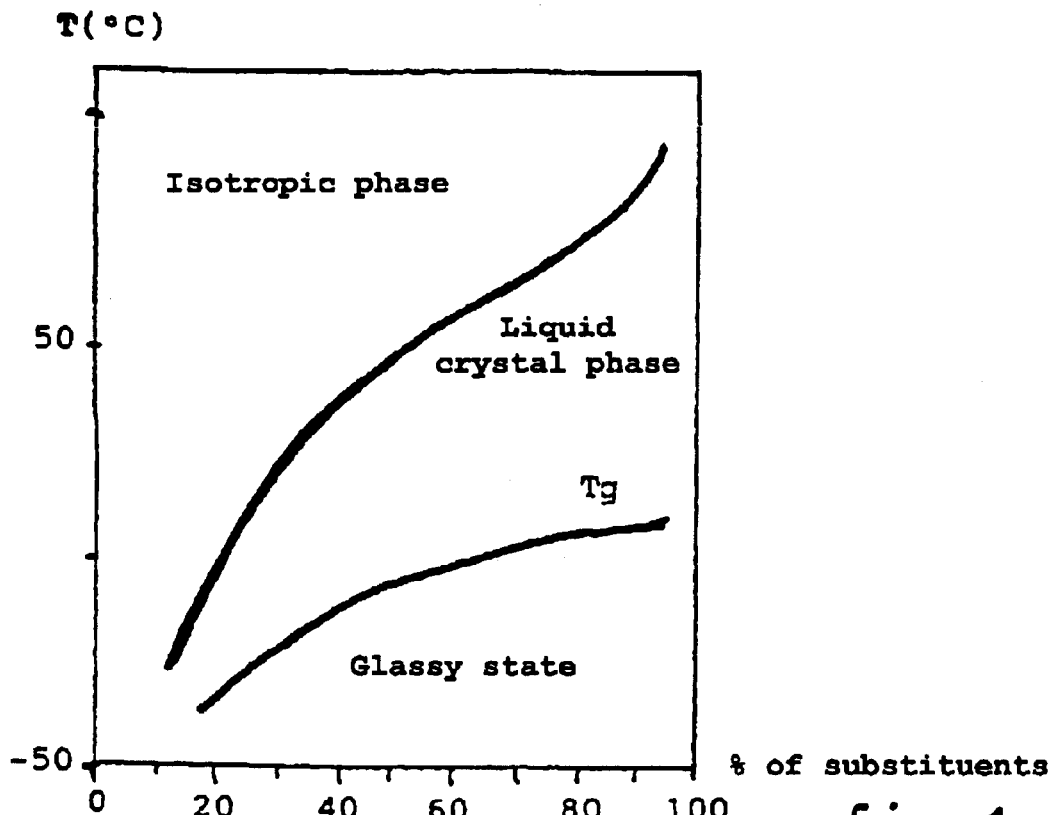

The present invention relates to optical systems, in particular centered optical systems such as intraocular lenses, contact lenses, etc.

BACKGROUND OF THE INVENTION

It is known that the human eye is a complex optical system whose role is to transmit to the brain the images arriving thereat. One of the essential components is the lens. The crystalline lens, located behind the iris, is a transparent gelatinous mass contained in the lens sac.

Opacification of the crystalline lens may occur with increasing age (cataract). All that can be done in that case is to remove the defective crystalline lens and replace it with an artificial crystalline lens or an intraocular lens.

The artificial crystalline lenses known to date are essentially made of acrylic materials, for example polymethyl methacrylate or copolymers thereof, or of silicone derivatives. They have relatively low refractive indices. For silicones, refractive indices of between 1.41 and 1.46 are currently available in the best of cases. For strong corrections, it is thus necessary to use intraocular lenses whose faces have a large curvature and which are consequently very thick in their optical axis.

In order to obtain the best correction without inducing astigmatism defects, it is also necessary to introduce the intraocular lens by making the smallest possible incision. To do this, flexible materials of the largest possible refractive index are sought so as to obtain a very thin intraocular lens.

In a healthy eye the crystalline lens is capable, under the action of muscles, the zonulae, which act upon the lens sac, of modifying its radius of curvature so as to adapt itself to close vision or distant vision.

Replacing the crystalline lens with an intraocular lens no longer allows accommodation to take place.

OBJECT OF THE INVENTION

One of the aims of the present invention is to produce an optical system such as an intraocular lens which overcomes the drawbacks of those of the prior art.

SUMMARY OF THE INVENTION

More specifically, the subject of the present invention is an optical system, in particular an intraocular lens or contact lens, characterized in that it is made of a material whose optical refractive index shows variations in at least one given direction.

According to one characteristic of the invention, the said material is a homogeneous material whose refractive index is variable as a function of its chemical composition.

According to another characteristic of the invention, the said material is a heterogeneous material with molecular orientations which vary in different zones.

According to another characteristic of the invention, the said material is a homogeneous material capable of modifying its optical refractive index when it is subjected to the action of external phenomena.

Another application is the production of bifocal contact lenses, allowing a simultaneous correction of two visual defects (for example myopia and presbyopia):

- either by juxtaposition of two materials, a central material and a peripheral material, of similar nature but of different indices, by means of different degrees of grafting onto the same matrix;
- or by juxtaposition of two different domains of the same material, the two domains having refractive indices that are different by virtue of a molecular orientation;
- or by producing a material whose index varies under the effect of a mechanical stress, for example the pressure of the eyelids.

BRIEF DESCRIPTION OF THE INVENTION

Figure 2:
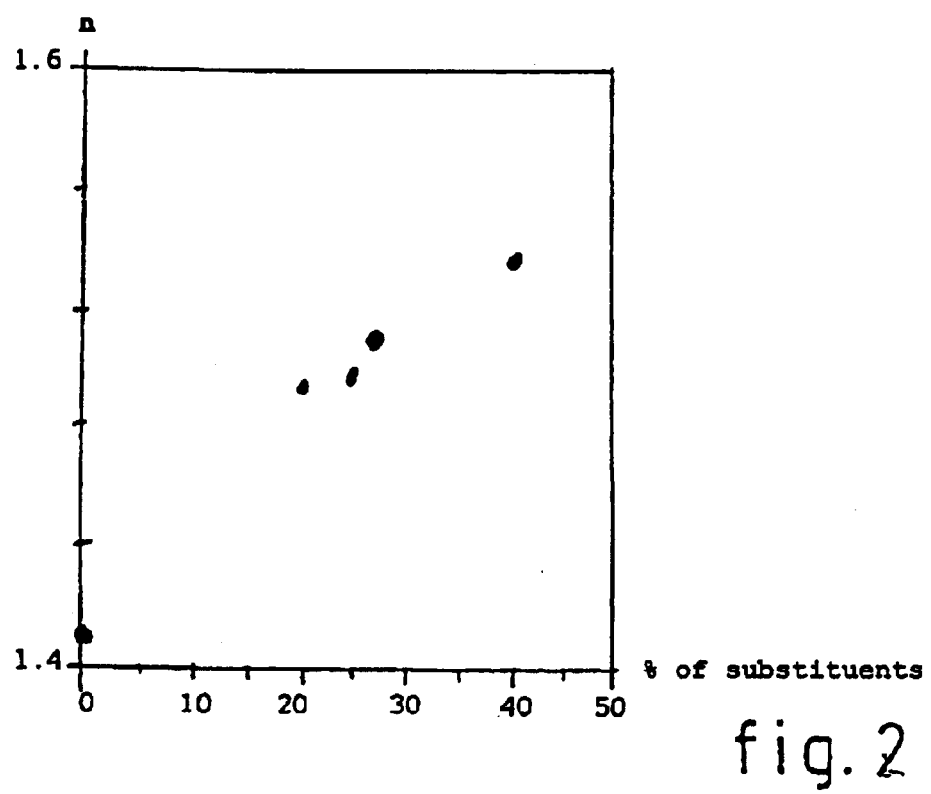

Other characteristics and advantages of the present invention will become apparent in the course of the description which follows, given with regard to the drawings attached for illustrative but in no way limiting purposes, in which:

FIGS. 1 and 2 represent graphs for explaining the variations in the properties of materials used to produce an optical system such as an intraocular lens according to the invention as a function of the composition of these materials, the graph in FIG. 1 showing the change in glass transition temperatures as a function of the content of substituents, and the graph in FIG. 2 showing the change in refractive index n as a function of the content of substituents.

DETAILED DESCRIPTION OF THE INVENTION

The optical system such as the intraocular lens according to the invention is made of a material whose optical refractive index shows variations in at least one given direction.

In a first embodiment, this material is homogeneous and has a high refractive index n which varies according to its chemical composition.

Specifically, for a given molecule, the molar refraction R is, to a first approximation, an additive function of the contributions of the various elements present in the molecule. Among the common chemical groups, those which have the greatest effects in increasing R are mainly sulfur, the halogens, in particular chlorine, bromine and iodine, and aromatic nuclei.

The refractive index n of the molecule increases as R increases, such that it is the molecules containing the elements mentioned above which have the largest indices.

Examples benzene n=1.498 o-dichlorobenzene n=1.551 carbon disulfide n=1.628 diiodomethane n=1.749

Similarly, the addition of groups of high refractive index n to a polymer increases the refractive index of the material.

By way of example, mention will be made of the case of silicon substituted with 9-vinylanthracene substituents. The refractive index of the material obtained increases as the content of substituents increases:

without substituent: n=1.403 with 94% substituents: n=1.690

The glass transition temperatures Tg also increase as the degree of substitution increases due to the rigidity of the aromatic nuclei:

without substituent: Tg=−130° C.

with 94% substituents: Tg=between 10° C. and 20° C.

The process for manufacturing the homogeneous material having a high refractive index n which is variable according to its chemical composition, and which is necessary for producing an intraocular lens according to the invention, comprises the following two steps:

Firstly, groups chosen from those described above, in particular aromatic nuclei whose presence also gives the material obtained the capacity to filter out ultraviolet radiation, which is an essential property for a high-quality intraocular lens, are fixed onto the polymers used for the lenses and artificial crystalline lenses, this fixing being obtained via a flexible portion so as to disrupt the temperature Tg as little as possible.

Examples
substituent of type [1]:

substituent of type [2]:

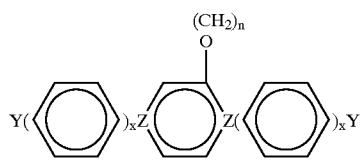

Next, the degree of substitution is modified continuously, and thus also the refractive index of the material, in order to obtain copolymers with a modulatable proportion of substituted units and of unsubstituted units. In the case of silicones, it is necessary to prepare the copoly(methylhydrogenodimethyl)siloxane of variable composition beforehand.

Two examples are given below, one starting with a silicone support, the other starting with an acrylate support, the substituent chosen corresponding to formula [1] above in which n=4, Z=OCO, Y=$OC_mH_{2m+1}$ with m=1 and x=1.

In the case of the first example, that with a silicone support, the substituent must have a vinyl end bonding group:

Example:

This group can be obtained in two steps: reaction of 4-bromobutene with hydroquinone, followed by esterification with p-methoxybenzoic acid.

The main siloxane chain has a random distribution of methylhydrogenosiloxane substitutable units and of dimethylsiloxane unsubstitutable units in variable proportion. These copolymers are obtained by acid-catalyzed redistribution of dimethylsiloxane units introduced in adequate amount via octamethylcyclotetrasiloxane and of methylhydrogenosiloxane units provided by homopolymethylhydrogenosiloxanes.

The substituent is fixed onto the main chain by hydrosilylation at 60° C. in the presence of a solvent. It is introduced in deficit relative to the methylhydrogenosiloxane units (from 5% to 15%) in order to allow a subsequent reaction of the excess units during the crosslinking step.

At the end of the hydrosilylation reaction, the polymer is freed of virtually all of the solvent by evaporation under vacuum at room temperature. It is then mixed with a crosslinking agent, and the rest of the solvent is evaporated off under vacuum.

The crosslinking agent is preferably a flexible chain and is terminated with two vinyl ends. Its proportion is such that the amount of vinyl bonding groups corresponds to the amount of methylhydrogenosiloxane units left free.

Example of a crosslinking agent:

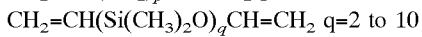

The polymer/crosslinking agent mixture is cast in a mold treated such that the material does not stick to the walls. The mold is placed at 60° C. in an oven for several hours in order to obtain a crosslinked polymer, which is removed from the mold.

This product can be washed by swelling it with a solvent, in order to remove any unreacted molecules, followed by drying it slowly.

In the second example, that with an acrylate support, the acrylate or methacrylate monomer, bearing the chosen substituent, must be synthesized:

Example:

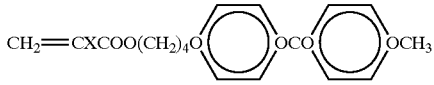

with X=H, $CH_3$

This group can be obtained in four steps: reaction of 4-bromobutanol in which the alcohol function has been protected, with hydroquinone; esterification with p-methoxybenzoic acid; deprotection of the alcohol function; esterification between this alcohol function and the carboxylic group of acrylic or methacrylic acid.

A bifunctional monomer containing an acrylate or methacrylate function at both ends must also be synthesized. It can be obtained according to the following scheme: reaction of 4-bromobutanol, in which the alcohol function has been protected, with hydroxybenzoic acid; esterification with the product of the reaction of 4-bromo-butanol, in which the alcohol function has been protected, with hydroquinone; deprotection of the alcohol functions; esterification of these alcohol functions with the carboxylic functions of acrylic or methacrylic acid.

Other bifunctional monomers can be used: ethylene glycol dimethacrylate; triethylene glycol dimethacrylate; tetraethylene glycol dimethacrylate; 1,6-hexanediol dimethacrylate; 1,12-dodecanediol dimethacrylate.

The polymerization is initiated by heating or UV irradiation in the presence of an initiator (for example azobisisobutyronitrile) or by any other common system (chemical accelerator, microwave irradiation).

The production of crosslinked materials with a variable proportion of substituents is possible by mixing, prior to the polymerization reaction, one or more unsubstituted monomers (methyl acrylate, methyl methacrylate or hydroxyethyl methacrylate, for example) with the above monofunctional and bifunctional monomers in suitable proportion. Hydroxyethyl methacrylate (HEMA) gives the material a hydrophilic nature until a degree of hydration of 40% for a homopolymer is obtained. Even more hydrophilic comonomers may be combined therewith, such as N-vinylpyrrolidone (VP) for example.

The lenses or crystalline lenses can be obtained either by machining the final materials or by carrying out the final step (polymerization/crosslinking) in a mold. When the base monomer has hydrophilic properties, the final material can be swollen in aqueous medium and become more or less pliable depending on its composition.

Compared with the base acrylates or silicones, the materials thus obtained have properties which allow the preparation of artificial crystalline lenses, intraocular lenses or contact lenses according to the invention.

Specifically, their refractive index n and their glass transition temperature Tg are higher and vary according to their chemical composition. In particular, they increase as the proportions of substituents increase.

One example of this change is illustrated in FIGS. 1 and 2 for the silicone materials whose method of synthesis has been given hereinabove.

In this example, the crosslinking agent is an alkyl chain; a crosslinking agent with three different chain lengths corresponding to 10, 16 or 22 carbons was studied; three different proportions of this crosslinking agent were introduced (5, 10 and 15%). These two parameters have little influence on the change in the refractive index or in the glass transition temperature, as may be seen in FIGS. 1 and 2.

On the other hand, the refractive index increases very rapidly as the content of substituents increases, FIG. 2, since with 40% substituents, indices above 1.53 are obtained.

The change in the glass transition temperature, FIG. 1, is slower. Even with total substitution, the Tg remains less than room temperature.

The mechanical properties are relatively unaffected by the substituents. For example, the modulus of elasticity under shear (G') at zero frequency:

unmodified silicone: $G'=10^5$ Pa silicone with more than 85% substituents: $G'=4\times10^4$ Pa

According to a second embodiment, the material of which the intraocular lens according to the invention is made is a heterogeneous material with a high and variable index in the material.

The aromatic substituents proposed above are thermotropic liquid crystals. They give the polymer bearing them mesomorphic properties, i.e., in particular, molecular orientation properties: within a given temperature range, these substituents very readily become oriented under the effect, for example, of a magnetic or electric field. This orientation is then "set" by the crosslinking process.

Under the orientation effect as mentioned above, the refractive index becomes anisotropic. It is thus possible, by orienting the substituents, to modify the refractive index in a given direction.

According to the present invention, the optical system is obtained from the same polymer, for example silicone or acrylate or methacrylate, by preparing batches with different indices obtained by orienting the substituents in different directions.

The orientations can be obtained by placing the substituted polymer (in the case of silicones) or the various monomers, substituted or unsubstituted (in the case of acrylates) in a weak magnetic field of about 1 Tesla or in an electric field, or by a surface treatment of the device allowing the material or lens to be manufactured in its final shape. The crosslinking (in the case of silicones) or the polymerization/crosslinking (in the case of acrylates) are carried out by heat treatment, for example, under this orientating field.

These batches of identical chemical nature are entirely compatible. They may be assembled so as to form lenses or crystalline lenses with different accommodation zones. For example, an intraocular lens may be produced in two parts: a central optical zone adapted for close vision and a peripheral zone adapted for distant vision.

According to a third embodiment, the material used to produce the optical system such as the intraocular lens according to the invention is a homogeneous material of high index which is variable by means of a mechanical effect, thereby allowing accommodation.

According to one characteristic of the invention, the material of which the optical system is made is a three-dimensional liquid crystal polymer whose mesomorphic portions can be readily oriented by means of a mechanical effect.

It is possible, for example, firstly to prepare crosslinked liquid crystal polymers without prior orientation of the mesogenic units. Using this material, artificial crystalline lenses or intraocular lenses will then be produced, for example by polymerization/crosslinking in a mold or by machining depending on the properties of the material. The zonulae exert a mechanical stress which is reflected, via the lens sac, onto the crystalline lens. This stress exerted by ocular tissue modifies the orientation of the liquid crystal substituents and thus the refractive index in the direction of vision. Similarly, in the case of contact lenses, a pressure from the eyelids can produce mechanical deformations needed for the molecular reorientation and thus vary the refractive index and consequently the power of the lens.

It is also possible to give these materials a pre-orientation of the substituents during their production, which preorientation will be modified under the effect of compressions or stretches transmitted to the sac via the zonulae.

In order for the material without preorientation of the mesogenic units to be transparent, or in order for a preoriented material to remain transparent after the disorientation, it is placed in isotropic phase under the conditions of use. Furthermore, in order to obtain a sufficient orientation under stress and thus a significant modification of the refractive index, it is necessary to carry out the process in a temperature range about 10° C. above the temperature $T_I$ at which the sample becomes isotropic. This obligation imposes an upper limit on the degree of substitution, as illustrated in FIG. 1. In the example chosen, a siloxane modified to about 35% would be entirely suitable for use: it is isotropic at about 35° C. with a refractive index of greater than 1.51 (FIG. 1).

In the isotropic phase, the index variation is proportionately greater the closer the temperature of use is to $T_I$. An example of the difference in index between two perpendicular directions, $\Delta n$, induced by a mechanical stress is given below. The compound chosen corresponds to a methacrylate substituted with various groups of type [2] defined above:

at $T_I+4°$ C. $\Delta n=6\times10^{-3}$ for a stress of $5\times10^{-2}$ N.mm$^{-2}$
$\Delta n=2\times10^{-3}$ for a stress of $2\times10^{-2}$ N.mm$^{-2}$ at $T_I+25°$ C. $\Delta n=1\times10^{-3}$ for a stress of $5\times10^{-2}$ N.mm$^{-2}$
$\Delta n=0.3\times10^{-3}$ for a stress of $2\times10^{-2}$ N.mm$^{-2}$

What is claimed is:

1. An ophthalmic lens device comprising a material having an optical refractive index varying in at least one direction in response to a force being exerted directly on the material by ocular tissue, for causing the refractive index to change, wherein said material comprises at least one polymer onto which is bonded at least one substituent selected from the group consisting of sulfur, halogens and aromatic nuclei.

2. An ophthalmic lens device comprising a material having an optical refractive index varying in at least one direction in response to a force being exerted directly on the material by ocular tissue, for causing the refractive index to change, wherein said material comprises at least one polymer onto which is bonded at least one substituent selected from the group consisting of chlorine, bromine and iodine.

3. The ophthalmic lens according to claim 1, wherein the polymer is a silicon or a polymer or a copolymer comprising an acrylate or methacrylate monomer.

4. The ophthalmic lens according to claim 2, wherein the polymer is a silicon or a polymer or a copolymer comprising an acrylate or methacrylate monomer.

5. An ophthalmic lens device comprising a material having an optical refractive index varying in at least one direction in response to a force being exerted directly on the material by ocular tissue, for causing the refractive index to change, wherein said material comprises at least one mesomorphic compound.

6. An ophthalmic lens device comprising a material having an optical refractive index varying in at least one direction in response to a force being exerted directly on the material by ocular tissue, for causing the refractive index to change, wherein said material comprises a liquid crystal polymer.

7. The ophthalmic lens device according to claim 6, wherein said liquid crystal polymer is a three-dimensional liquid crystal polymer.

8. The ophthalmic lens device according to claim 6, wherein said liquid crystal polymer is a three-dimensional liquid crystal polymer having mesomorphic portions capable of being oriented by means of a mechanical effect.

9. The ophthalmic lens device according to claim 1, wherein said material comprises portions capable of being oriented by means of a mechanical effect.

10. The ophthalmic lens device according to claim 2, wherein said material comprises portions capable of being oriented by means of a mechanical effect.

11. The ophthalmic lens device according to claim 5, wherein said material comprises portions capable of being oriented by means of a mechanical effect.

12. The ophthalmic lens device according to claim 6, wherein said material comprises portions capable of being oriented by means of a mechanical effect.

13. The ophthalmic lens device according to claim 1, wherein said material has an optical refractive index varying in at least one direction in response to a force exerted by a muscle of the eye.

14. The ophthalmic lens device according to claim 2, wherein said material has an optical refractive index varying in at least one direction in response to a force exerted by a muscle of the eye.

15. The ophthalmic lens device according to claim 5, wherein said material has an optical refractive index varying in at least one direction in response to a force exerted by a muscle of the eye.

16. The ophthalmic lens device according to claim 6, wherein said material has an optical refractive index varying in at least one direction in response to a force exerted by a muscle of the eye.

17. The ophthalmic lens device according to claim 1, wherein said material has an optical refractive index varying in at least one direction in response to a force exerted by the zonulae.

18. The ophthalmic lens device according to claim 2, wherein said material has an optical refractive index varying in at least one direction in response to a force exerted by the zonulae.

19. The ophthalmic lens device according to claim 5, wherein said material has an optical refractive index varying in at least one direction in response to a force exerted by the zonulae.

20. The ophthalmic lens device according to claim 6, wherein said material has an optical refractive index varying in at least one direction in response to a force exerted by the zonulae.

21. The ophthalmic lens device according to claim 1, wherein said material has an optical refractive index varying in at least one direction in response to a force exerted by an eyelid.

22. The ophthalmic lens device according to claim 2, wherein said material has an optical refractive index varying in at least one direction in response to a force exerted by an eyelid.

23. The ophthalmic lens device according to claim 5, wherein said material has an optical refractive index varying in at least one direction in response to a force exerted by an eyelid.

24. The ophthalmic lens device according to claim 6, wherein said material has an optical refractive index varying in at least one direction in response to a force exerted by an eyelid.

25. The ophthalmic lens device according to claim 1, wherein said ophthalmic lens device is a contact lens.

26. The ophthalmic lens device according to claim 2, wherein said ophthalmic lens device is a contact lens.

27. The ophthalmic lens device according to claim 5, wherein said ophthalmic lens device is a contact lens.

28. The ophthalmic lens device according to claim 6, wherein said ophthalmic lens device is a contact lens.

29. The ophthalmic lens device according to claim 1, wherein said ophthalmic lens device is an intraocular lens.

30. The ophthalmic lens device according to claim 2, wherein said ophthalmic lens device is an intraocular lens.

31. The ophthalmic lens device according to claim 5, wherein said ophthalmic lens device is an intraocular lens.

32. The ophthalmic lens device according to claim 6, wherein said ophthalmic lens device is an intraocular lens.

33. The ophthalmic lens device according to claim 1, wherein said material has portions whose orientation is responsive to force exerted by ocular tissue.

34. The ophthalmic lens device according to claim 2, wherein said material has portions whose orientation is responsive to force exerted by ocular tissue.

35. The ophthalmic lens device according to claim 5, wherein said material has portions whose orientation is responsive to force exerted by ocular tissue.

36. The ophthalmic lens device according to claim 6, wherein said material has portions whose orientation is responsive to force exerted by ocular tissue.

* * * * *